United States Patent [19]

Seyedin et al.

[11] Patent Number: 4,627,982

[45] Date of Patent: * Dec. 9, 1986

[54] PARTIALLY PURIFIED BONE-INDUCING FACTOR

[75] Inventors: Saeid Seyedin, Mountain View; Thomas Thomas, Davis, both of Calif.

[73] Assignee: Collagen Corporation, Palo Alto, Calif.

[*] Notice: The portion of the term of this patent subsequent to Feb. 28, 2001 has been disclaimed.

[21] Appl. No.: 705,479

[22] Filed: Feb. 26, 1985

Related U.S. Application Data

[63] Continuation-in-part of Ser. No. 630,938, Jul. 16, 1984, abandoned.

[51] Int. Cl.$^4$ .............................................. A61K 35/32
[52] U.S. Cl. ................... 424/95; 260/112 R; 260/123.7; 435/68; 435/69; 435/70; 435/268; 106/122; 106/161; 424/15; 514/21; 514/801; 530/416; 530/417
[58] Field of Search ............... 260/112 R, 123.7; 424/95, 15; 435/268, 68, 69, 70

[56] References Cited

U.S. PATENT DOCUMENTS

| | | | |
|---|---|---|---|
| 3,458,397 | 7/1969 | Myers et al. | 435/268 X |
| 4,294,753 | 10/1981 | Urist | 260/112 R |
| 4,394,370 | 7/1983 | Jefferies | 260/123.7 X |
| 4,434,094 | 2/1984 | Seyedin et al. | 260/112 R |
| 4,440,750 | 4/1984 | Glowaeki et al. | 424/95 |
| 4,455,256 | 6/1984 | Urist | 260/112 R |
| 4,485,097 | 11/1984 | Bell | 424/95 |
| 4,488,911 | 12/1984 | Luck et al. | 106/161 |
| 4,563,350 | 1/1986 | Nathan et al. | 424/95 |

OTHER PUBLICATIONS

Reddi et al. Proc. Natl. Acad. Sci. USA (1972), 69:209–226.
Urist, Clin. Orthop. Rel. Res. 162 (1982), 219–232.
Urist et al. Science, 220, 680–686 (1983).
Urist et al. Proc. Natl. Acad. Sci. USA (1984), 81:371–375.
Journal of Biol. Chem., 256, 10403–10408, Termine et al.
Hanamura et al. Clin. Orthop. Rel. Res. 153, 232–240 (1980).

Primary Examiner—Howard E. Schain
Attorney, Agent, or Firm—Ciotti & Murashige

[57] ABSTRACT

A partially purified proteinaceous bone-inducing factor of 10,000 to 30,000 daltons is described. It is derived from demineralized bovine bone by extraction with a chaotropic agent, gel filtration, cation exchange chromatography using carboxymethyl cellulose at pH 4.8 and gradient elution with NaCl at 10 mM to about 150 mM.

8 Claims, 6 Drawing Figures

SPECIFIC CHONDROGENIC IN VITRO ACTIVITY OF LMW – PROTEINS

| FRACTION (OFE) | PROTEIN % YIELD | SPECIFIC ACTIVITY UNITS/mg | RATIOS IN R-DBP | % OFE IN R-DBP |
|---|---|---|---|---|
| BONE EXTRACT | 100 | 43.5 | – | – |
| CMC-BOUND | 1.8 | 1600 | 1:148 | 0.67 |
| CMC-B-1 | 0.135 | 870 | 1:62 | 1.6 |
| CMC-B-2 | 0.0129 | 16 700 | 1:11150 | 0.087 |
| CMC-B-3 | 0.0346 | 13 640 | 1:500 | 0.2 |
| CIF-A | 0.071 | 169 000 | 1:6730 | 0.015 |
| CIF-B | 0.0013 | 465 000 | 1:2500 | 0.004 |

PARTIALLY PURIFIED BONE-INDUCING FACTOR

CROSS-REFERENCE TO RELATED APPLICATION

This application is a continuation-in-part of copending U.S. patent application Ser. No. 630,938, filed July 16, 1984, now abandoned.

DESCRIPTION

1. Technical Field

The present invention relates to protein chemistry and osteoplasty. More particularly, it relates to a partially purified proteinaceous factor that promotes rapid bone growth.

2. Background Art

It has been established that bone contains materials which can stimulate the formation of new bone when placed in contact with living systems. (Urist, M. R., Clin Orthop (1968) 56:37; Science (1965) 150:893; Reddi, A. H., et al, Proc Natl Acad Sci (USA) (1972) 69:1601.) Attempts have been made to purify whatever factors are responsible for this activity. A "bone morphogenic protein" (BMP) was extracted from demineralized bone using urea or guanidine hydrochloride and reprecipitated according to the disclosures in U.S. Pat. Nos. 4,294,753 and 4,455,256 to Urist. Urist subsequently reported (Urist, M. R., Clin Orthop Rel Res (1982) 162:219) that ion exchange purification of this crude protein mixture yielded an activity which was unadsorbed to carboxymethyl cellulose (CMC) at pH 4.8. Urist's most recent reports (Science (1983) 220:680–685 and Proc Natl Acad Science (USA) (1984) 81:371–375) describe BMPs having molecular weights of 17,500 and 18,500 daltons.

U.S. Pat. No. 4,434,094 to Seyedin and Thomas reported the partial purification of what is evidently a bone generation-stimulating, bone-derived protein by extraction with chaotropic agents, fractionation on anion and cation exchange columns, and recovery of the activity from a fraction adsorbed to CMC at pH 4.8. This new protein fraction was termed "osteogenic factor" (OF) and was characterized as having a molecular weight below about 30,000 daltons and as tracking the purification process described. The two porteins of parent application Ser. No. 630,938 were purified to homogeneity using a purification procedure that is similar in part to that disclosed in U.S. Pat. No. 4,434,094. Those two proteins eluted from CMC resin at about a 150–200 mM NaCl gradient. The present application concerns a bone inducing factor present in the CMC-bound fraction that elutes from the resin in the portion of the NaCl gradient below about 150 mM.

Three major approaches are available to the problem of bone replacement. One is a strictly mechanical approach whereby missing or defective bone is replaced by an alloimplant that is intended to mimic the function of the natural bone. This approach, while simple in concept, is unsuccessful in practice as the alloimplant requires integration with the normal skeletal system. Alternatively, the missing portion of osseous tissue may be temporarily substituted by a matrix which permits the ingrowth of the subject's own tissue and thus effects the desired integration over a short period of time. It has become clear that such matrices can operate in two fundamentally complementary ways: the implant may simply provide a passive support around which new bone growth occurs or the matrix may be complemented by a material which actively induces the ingrowth of new bone. The latter process, termed osteoinduction, may require a cartilage intermediate. Thus, any osteogenic factor may also be chondrogenic and vice versa.

DISCLOSURE OF THE INVENTION

The invention relates to methods for obtaining a partially purified bone inducing factor from demineralized bone (DMB), the factor prepared thereby, implant materials containing the factor, and methods for inducing bone formation in mammals using the factor.

The purification method involves:

(a) extracting demineralized bone with a chaotropic (dissociative) extractant that solubilizes nonfibrous proteins;

(b) subjecting the extract from step (a) to gel filtration to recover a fraction containing proteins of molecular weight 10,000–30,000 daltons;

(c) adsorbing the fraction from step (b) onto a carboxymethyl cellulose cation exchanger at approximately pH 4.5–5.5; and (d) eluting an osteogenically active fraction from the cation exchanger with a sodium chloride gradient of about 10 mM to about 150 mM.

The osteogenic implant material comprises:

(a) an effective amount of the above-described osteogenic factor reconstituted with (b) a substantially nonimmunogenic carrier.

The method of inducing bone formation at a predetermined site in a living mammal comprises implanting the above-described implant material at said site.

MODES OF CARRYING OUT THE INVENTION

The native sources of the bone-inducing factor of the claimed invention are bone, dentin, osterosarcomas or chondrosarcomas. In view of the showing that bone inductive proteins from human, monkey, bovine and rat are non-species specific in their ability to produce endochondral bone in xenogeneic implants (Sampath, T. K., et al, Proc Natl Acad Sci (USA) (1983) 80:6591) it is believed that the factor of the claimed invention has been highly conserved among mammalian species (i.e., factors from different mammalian species will have substantially homologous amino acid sequences that vary, if at all, in one or more amino acid residue additions, deletions, or substitutions that do not affect the non-species specific bone inducing activity of the molecule adversely). In this regard the terms "substantially equivalent" and "substantially homologous" as used herein are intended to mean factors regardless of species, that have the same amino acid composition or sequence, as the case may be, of the factor described in the example and factors of similar but different amino acid composition or sequence, which difference(s) does not affect non-species specific endochondral bone-inducing activity adversely. Accordingly, such factors may be derived from cells or tissue of diverse mammalian origin. The source of factor prepared by purification from native sources is advantageously porcine or bovine long bone because of its ready availability.

A variety of initial preparation procedures are possible, but basically the bone is first cleaned using mechanical or abrasive techniques, fragmented, and further washed with, for example, dilute aqueous acid preferably at low temperature, and then defatted by extraction with a lipophilic solvent such as ether or ethyl acetate. The bone is then demineralized by removal of the calcium phosphates in their various forms, usually by extraction with stronger acid. These techniques are understood in the art, and are disclosed, for example, in U.S. Pat. No. 4,434,094. The resulting preparation, a demineralized bone, is the starting material for the preparation of the claimed osteogenic factor.

The initial extraction is designed to remove the non-fibrous (e.g., non-collagenous) proteins from the demineralized bone. This can be done with the use of chaotropic agents such as guanidine hydrochloride (at least about 4 molar), urea (8 molar) plus salt, or sodium dodecylsulfate (at least about 1% by volume) or such other chaotropic agents as are known in the art (Termine, et al, *J Biol Chem* (1980) 255: 9760–9772; and Sajera and Hascall, *J Biol Chem* (1969) 244: 77–87 and 2384–2396). The extraction is preferably carried out at reduced temperatures in the presence of a protease inhibitor to reduce the likelihood of digestion or denaturation of the extracted portein. Examples of protease inhibitors that may be included are phenylmethylsulfonylfluoride (PMSF) sodium azide, N-ethyl maleimide (NEM), benzamidine, and 6-amino hexanoic acid. The pH of the medium depends upon the extractant selected. The process of extraction generally takes on the order of about 4 hr to 1 day.

After extraction, the extractant may be removed by suitable means such as dialysis against water, preceded by concentration by ultrafiltration if desired. Salts can also be removed by controlled electrophoresis, or by molecular sieving, or by any other means known in the art. It is also preferred to maintain a low temperature during this process so as to minimize denaturation of the proteins. Alternatively, the extractant chaotropic agent need not be removed, but rather the solution need only be concentrated, for example, by ultrafiltration.

The extract, dissolved or redissolved in chaotropic agent, is subjected to gel filtration to obtain fractions of molecular weight below about 30,000 daltons, thus resulting in a major enhancement of purity. Gel sizing is done using standard techniques, preferably on a Sephacryl column at room (10° C.–25° C.) temperature.

The low molecular weight fraction is then subjected to ion exchange chromatography using CMC at approximately pH 4.5–5.2, preferably about 4.8, in the presence of a nonionic chaotropic agent such as 6M urea. Other cation exchangers may be used, including those derived from polyacrylamide and cross-linked dextran; however cellulosic cation exchangers are preferred. Of course, as in any ion exchange procedure, the solution must be freed of competing ions before application to the column. The factor is adsorbed on the column and is eluted in an increasing salt concentration gradient in the range of about 10 mM to about 150 mM.

The 10 mM–150 mM NaCl fraction from the cation exchange column may be subjected to RP-HPLC or nondenaturing gel electrophoresis for further purification.

The presence of the factor in the 10 mM–150 mM NaCl fraction is confirmed using an in vivo bone-induction assay described in detail below.

EXAMPLE

The following example is intended to illustrate the process for purification as applied to a particular sample. It is not intended to limit the invention.

A. PREPARATION OF DEMINERALIZED BONE

Fresh bovine metatarsal bone was obtained fresh from the slaughterhouse and transported on dry ice. The bones were cleaned of marrow and non-bone tissues, broken in fragments smaller than 1 cm diameter, and pulverized in a mill at 4° C. The pulverized bone was washed twice with 9.4 liters of double distilled water per kg of bone for about 15 min each, and then washed overnight in 0.01N HCl at 4° C. Washed bone was defatted using 3×3 volumes ethanol, followed by 3×3 volumes diethylether, each washed for 20 min, and all at room temperature. The resulting defatted bone powder was then demineralized in 0.5N HCl (25 l/kg defatted bone) at 4° C. The acid was decanted and the resulting DMB washed until the wash pH was greater than 4, and the DMB dried on a suction filter.

B. EXTRACTION OF NONCOLLAGENOUS PROTEINS

The DMB as prepared in paragraph A was extracted with 3.3 l of 4M guanidine-HCl, 10 mM ethylenediaminetetraacetic acid (EDTA), pH 6.8, 1 mM PMSF, 10 mM NEM per kg for 16 hr, the suspension suction filtered and the non-soluble material extracted again for 4 hr. The soluble fractions were combined and concentrated at least 5-fold by ultrafiltration using an Amicon ultrafiltration (10K) unit, and the concentrate dialyzed against 6 changes of 35 volumes cold deionized water over a period of 4 days, and then lyophilized. All of the procedures of this paragraph were conducted at 4° C. except the lyophilization which was conducted under standard lyophilization conditions.

C. GEL FILTRATION

Figure 1:
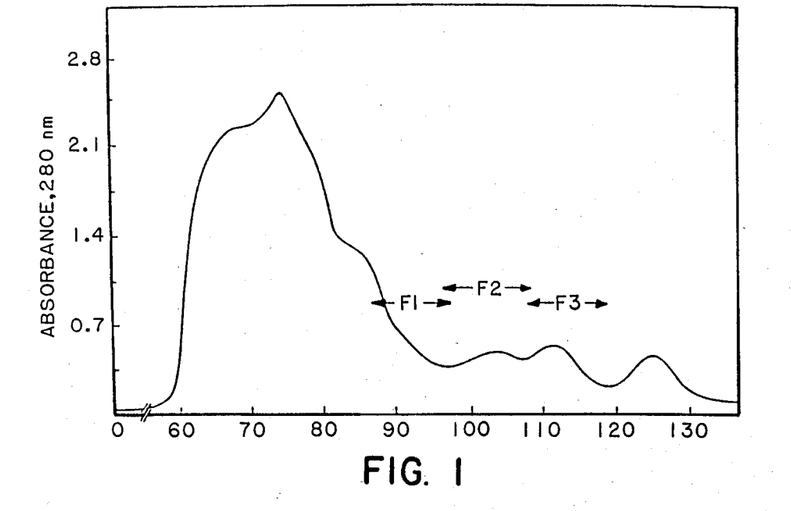
FIG. 1 is a graph of the optical densities (absorbances) (280 nm) of the gel filtration fractions of the example (paragraph C)

The extract from paragraph B, redissolved in 4M guanidine-HCl, was fractionated on a Sephacryl S-200 column equilibrated in 4M guanidine-HCl, 0.02% sodium azide, 10 mM EDTA, pH 6.8. Fractions were assayed by their absorbance at 280 nm and the fractions were combined as shown in FIG. 1. Fraction F2 of FIG. 1, constituting a low molecular weight (LMW, 10,000–30,000 daltons) protein fraction possessing the greatest activity was dialyzed against 6 changes of 180 volumes of deionized water and lyophilized. All operations except lyophilization and dialysis (4° C.) were conducted at room temperature.

D. ION EXCHANGE CHROMATOGRAPHY

Figure 2:
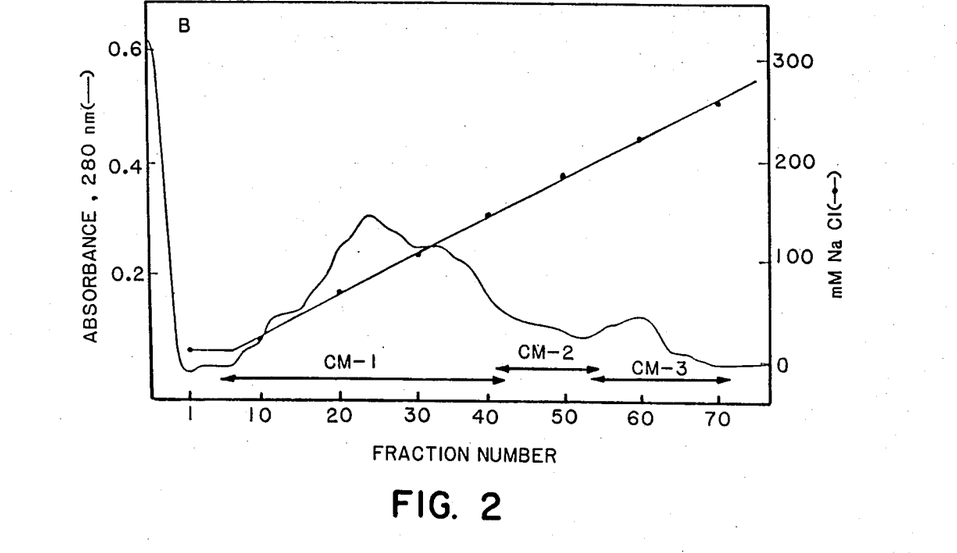
FIG. 2 is a graph of the optical densities (280 nm) of eluate fractions from the preparative ion exchange chromatography of the example (paragraph D)

Fraction F2 from paragraph C was dissolved in 6M urea, 10 mM NaCl, 1 mM NEM, 50 mM sodium acetate, pH 4.8 and centrifuged at 10,000 rpm for 5 min. The supernatant was fractionated on a CM52 (a commercially available CMC) column equilibrated in the same buffer. Bound proteins were eluted from the column using a 10 mM to 400 mM NaCl gradient in the same buffer, and a total volume of 350 ml at a flow rate of 27 ml/hr. Three major fractions, designated CM-1, CM-2 and CM-3, were collected as shown in FIG. 2. Each fraction was dialyzed against 6 changes of 110 volumes of deionized water for 4 days and lyophilized. All of the foregoing operations were conducted at room temperature except dialysis (4° C.).

E. RP-HPLC

The lyophilized fractions CM-2 and CM-3 from paragraph D were each dissolved in 0.1% trifluoroacetic acid (TFA) and aliquots of the solution loaded onto a Vydac C18 RP-HPLC column (4.6 mm ID×25 cm) and washed with 0.1% TFA for 5 min at 1 ml/min. The eluting solvent was a 0%–60% acetonitrile gradient in 0.1% TFA at a rate of 2%/min. Two peaks were obtained—peak A at about 29.5 min and peak B at about 31.3 min.

F. ASSAY FOR CHONDROGENIC ACTIVITY

The presence of the desired proteins in the fractions during purification was confirmed using an in vitro assay for the production of proteoglycans (PG), the identity of which was confirmed by enzyme-linked immunosorbent assay (ELISA). The assay is an agarose gel culture model using leg muscle cells isolated from rat fetuses. It assesses the ability of the samples to induce the production of cartilage specific PGs. The correlation between in vitro cartilage induction and in vivo bone formation has been shown by Seyedin, S., et al, *J Cell Biol* (1983) 97: 1950–1953.

The cell culture was prepared by removing muscle tissue aseptically from the upper limbs of nineteen-day-old Sprague Dawley rat fetuses, mincing the tissue, and culturing it in Eagle's Minimum Essential Medium (MEM) with 10% fetal bovine serum (FBS) and 50 units penicillin, 50 μg streptomycin per ml. Cellular outgrowth usually reached confluency within one week, whereupon cells were trypsinized, split 1:2 and used for experimentation within the first three passages.

The cells were placed in agarose gel cultures either with control medium or with samples to be tested. The procedure was basically that of Benya, et al, *Cell* (1982) 30: 215. Briefly, the cell monolayers were harvested by trypsinization, counted on a hemocytometer, and resuspended at two times the final cell concentration in the medium with or without the protein fraction to be tested. The control medium was either Hams F12, Dulbecco's Minimum Essential Medium (DMEM) or CMRL 1066 (Gibco) each containing 10% FBS and antibiotics. The test protein fractions in 0.01N HCl were diluted directly to the desired concentration of test protein diluted with an equal volume with 1% low melting agarose (Bio-Rad, #162-0017) in F-12, and 0.2 ml of the dilution was plated on 17 mm wells coated with 0.15 ml of 1% high melting (Bio-Rad, 190 162-0100) agarose. The resulting cultures were incubated at 37° C. for 5 min, chilled at 4° C. for 10 min, and then overlayed with 1 ml of the corresponding medium (control or test protein). The cells were then cultured in a humidified atmosphere of 5% $CO_2$, 95% air and fed every 3–4 days thereafter by a complete change with control medium. After 7 days the cultures were frozen and stored at −80° C. before assay.

The cultures were assayed by thawing at 4° C., homogenizing in 4M guanidine-HCl with 50 mM Na acetate, 13 mM EDTA, 6 mM NEM, and 3 mM PMSF at pH 5.8, and extracting by shaking overnight at 4° C. The supernatant fraction from centrifugation at 25,000×g for 40 min at 4° C. was dialyzed overnight at 4° C. against 50 volumes 0.2M NaCl, 50 mM Tris, pH 7.4. The supernatant was assayed for proteoglycans by ELISA as described by Renard, et al, *Anal Biochem* (1980) 104: 205, and in U.S. Pat. No. 4,434,094.

Briefly, for the ELISA, antiserum to cartilage PGs was raised in rabbits using standard techniques which showed no cross-reactivity with hyaluronic acid or PGs extracted from rat bone. Purified proteoglycn (Seyedin, S., et al, spura) from Swarm rat chondrosarcoma tissue was used as standard antigen. The dialyzed samples were diluted 1:1 (v/v) in phosphate-buffered saline (PBS) with 0.05% Tween 20, 1 mg/ml bovine serum albumin (BSA), pH 7.2 for assay. horseradish peroxidase conjugated goat anti-rabbit IgG (Tago) was the second antibody with o-phenylenediamine as substrate.

Figure 3A:
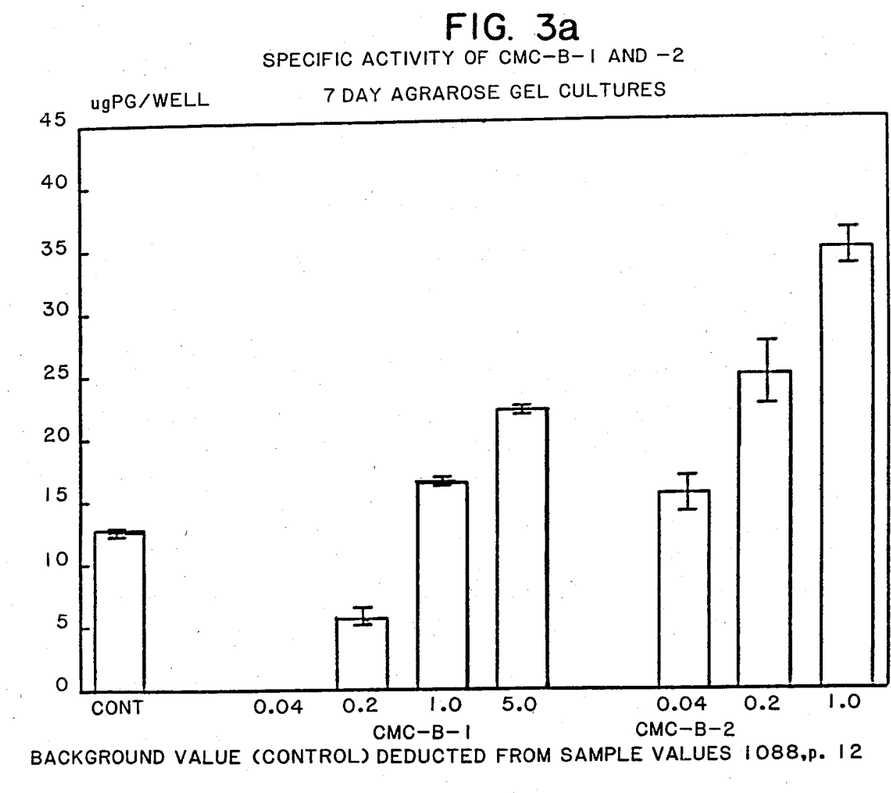
FIGS. 3(a) and 3(b) are graphs showing the specific chondrogenic activity as determined per paragraph F of certain proteins described in the example.
Figure 3B:
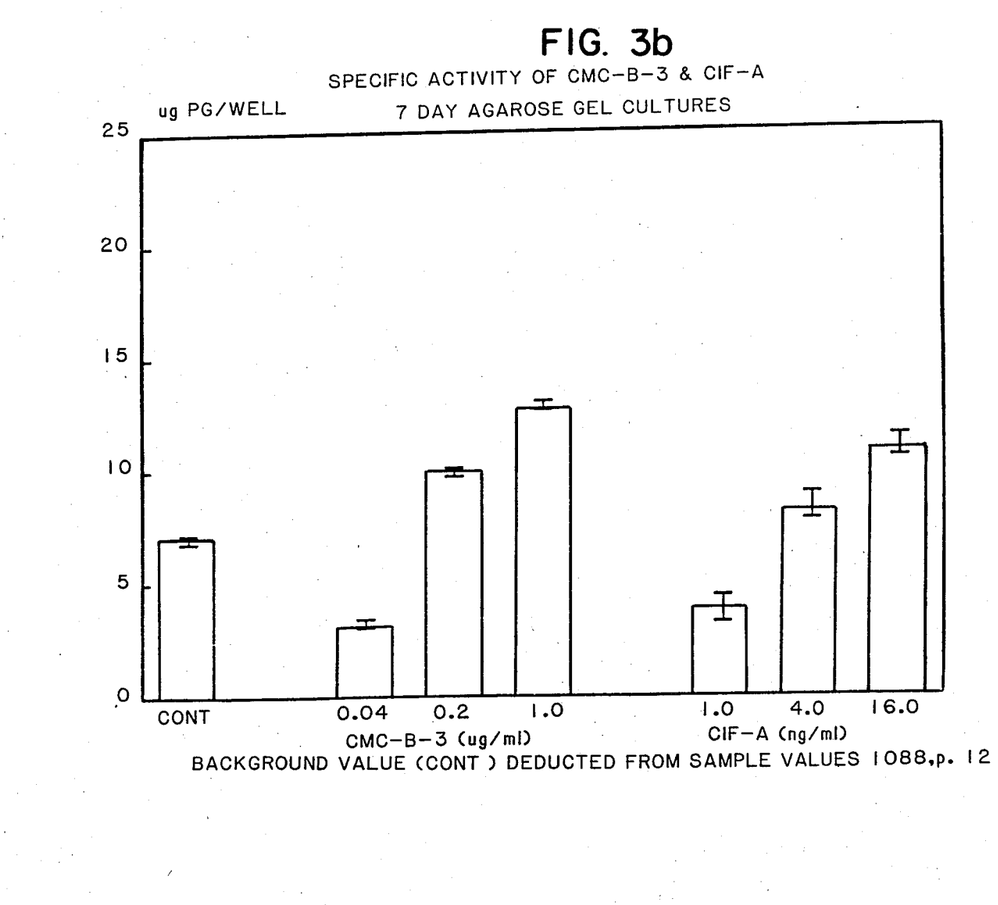

The results of the ELISA of the three CM-bound fractions from paragraph D (designated CMC-B-1, CMC-B-2, and CMC-B-3) and the protein of peak A (designated CIF-A) from paragraph E are shown in FIGS. 3(a) and 3(b).

G. RECONSTITUTION PROCEDURE

Figure 4:
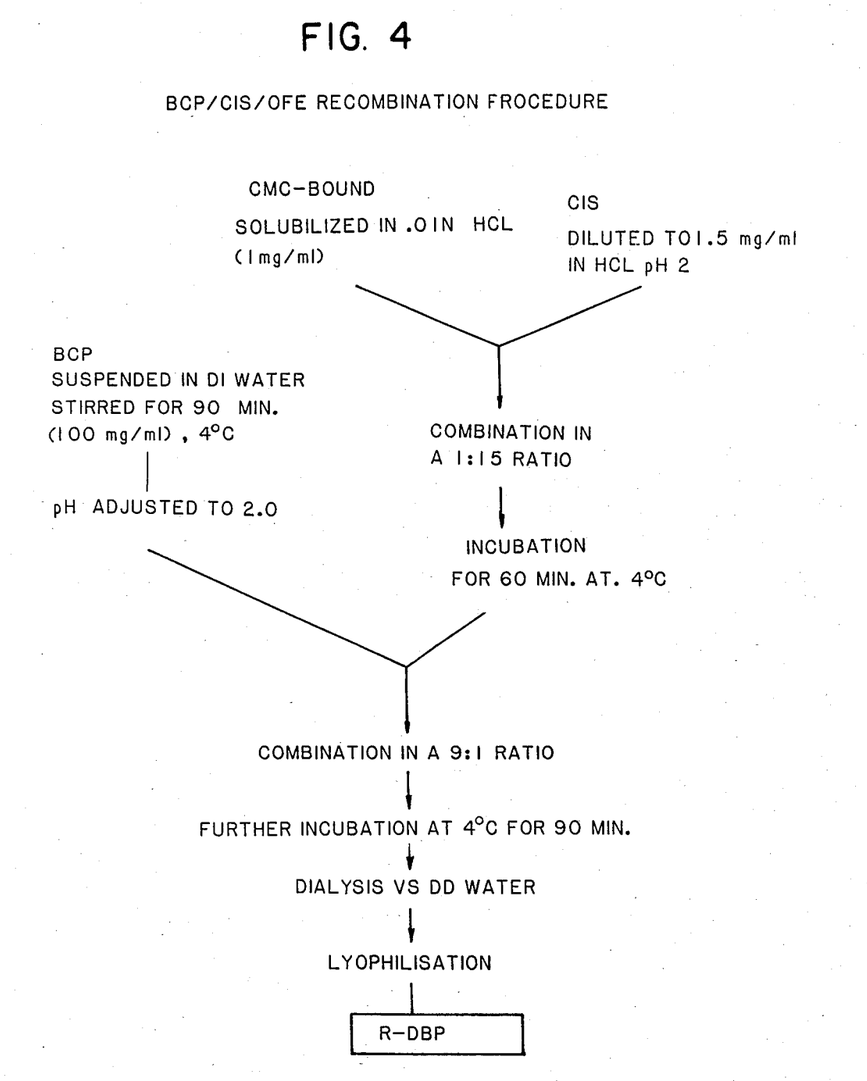
FIG. 4 is a schematic diagram outlining the reconstitution procedure described in paragraph G of the example.
Figure 5:
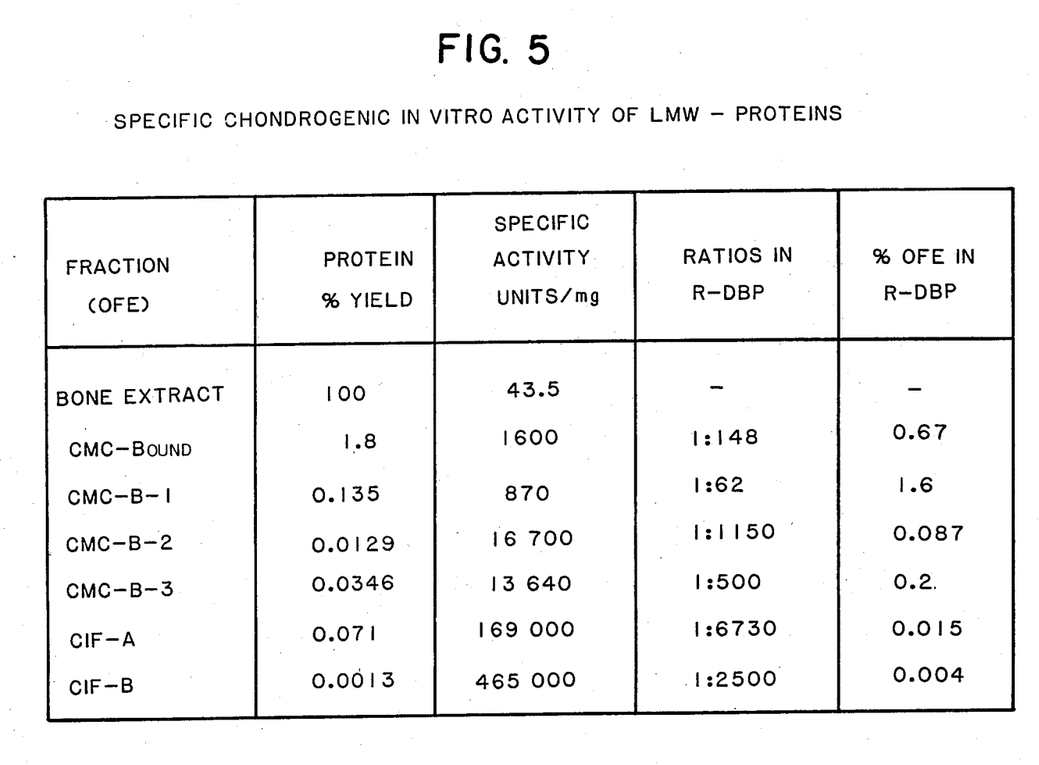
FIG. 5 is a table that provides details of the reconstituted samples described in paragraph G and their specific condrogenic activity as determined by the assay of paragraph F.

For reconstitution, the proteins prepared in the above described manner were combined with a 9:1 weight ratio mixture of bone collagen powder (BCP, lyophilized solids from paragraph C) and collagen in solution (CIS, available commercially from Collagen Corporation, Palo Alto, Calif. under the trademark ZYGEN ®) containing 10% native soluble bovine skin collagen by weight in ratios according to their in vitro chondrogenic activities. The procedure is depicted schematically in FIG. 4 and details of the compositions of the reconstituted (R) materials are reported in the Table shown in FIG. 5. According to this method all the reconstituted samples contained approximately an equal number of units of chondrogenic activity (about 1000 units/100 mg R-DBP). Only for CIF-A the dosage was doubled and CMC-B-1 was reconstituted in two different dosages. The protein content of CMC-B-1 was determined by Biuret assay and the one of all the other samples was measured by integration of the HPLC peaks compared to the peak area of a known bovine serum albumin standard at 220 nm. In case of pure CIF-A and CIF-B the HPLC fractions were directly added to the CIS solution before mixing with BCP. Also, a control sample consisting of the BCP/CIS carrier was prepared under the same conditions.

H. BIOASSAY SYSTEM

The osteoinductive abilities of samples were assayed by their ability to induce endochondral bone formation in the subcutaneous tissue of young male Sprague-Dawley rats. The samples were wetted with two volumes of sterile double distilled water (v/w), thoroughly mixed, packed in a 1 cc syringe, cut and weighed. All the samples were implanted on the ventral thoracic region, one on each side of the animal. Explants were removed after 14 and 28 days and evaluated biochemically and histologically.

I. HISTOLOGY STUDIES

Explants which had been removed after 14 and 28 days were subjected to histological assessment by fixing in 10% neutral formalin for 26 hr, and then processing for paraffin embedding. Four-six micron sections were taken from the imbedded tissues and were subsequently stained with either hematoxylin-eosin (general cytology), with safronin-O (proteoglycans) and Gomori trichrome (collagen).

J. BIOCHEMICAL ASSAYS

The 14 day explants were split in half, the wet weight determined and frozen at −80° C. till processed. The samples were first extracted and assayed for alkaline phosphatase activity and subsequently extracted and assayed for cartilage-specific proteoglycans. The right side 28 day explants were extracted and assayed first for alkaline phosphatase and then for calcium. The extraction and assay procedures are described below.

J.1. Proteoglycan Assay

Cartilage proteoglycan was assayed by an ELISA technique. The explants were weighed immediately after removal and frozen at −70° C. until extraction. For the extraction, the explants were cut into slices, and homogenized in ice cold extraction buffer in a Tekmar Tissuemizer for two 30 sec bursts at maximum setting. The extraction buffer was 6M guanidine hydrochloride, 75 mM sodium acetate or 4M guanidine hydrochloride, 50 mM acetate both containing 20 mM EDTA, 1 mM PMSF and 10 mM NEM at pH 5.8. Buffer was used in a 10:1 volume to the weight of the explant extracted, and the samples were incubated overnight (20 hr) at 4° C. The samples were then centrifuged at 12,000 rpm for 1 hr at 4° C., and the supernatants dialyzed overnight at 4° C. against 50 volumes of 50 mM Tris, 200 mM NaCl, pH 7.4. The dialyzate was subjected to ELISA performed as described by Renard, et al, *Arch Biochem Biophys* (1980) 207: 399 and by Seyedin, S., et al, *J Cell Biol* (1983) 97: 1950 using polystyrene microplates (Flow Laboratories, McClean, Va.). The antisera and the proteoglycan standard were prepared from Swarm rat chondrosarcoma tissue as described by Seyedin, S., et al, (supra). Horseradish peroxidase conjugated goat anti-rabbit IgG was used as the second antibody, samples were assayed in different solutions in PBS, 0.05% Tween 20, 1 mg/ml BSA and quantitated by use of the inhibition ELISA described by Shuures, et al, *Clin Chim* (1977) 81: 1.

J.2. Extractable Calcium

The formation of bone was also assessed by determination of calcium. The explants were cut in small pieces and suspended in 1:10 (m/v) of 0.5N HCl to dissolve the ions. The samples were incubated for another 5 days at room temperature and centrifuged at 12,000 rpm for 40 min. The calcium concentration of the supernatant was determined by atomic adsorption (Trace Analysis Laboratory, Hayward, Calif.).

J.3. Analysis for Alkaline Phosphatase

To determine alkaline phosphatase (AP), the explants were cut in small pieces and homogenized in 10 volumes (1/10) of ice cold 1.5M NaCl, 3 mM NaHCO$_3$, pH 7.5. The homogenized samples were then centrifuged at 12,000 rpm for 50 min at 4° C., and an aliquot of the supernatant diluted 1:10 in cold distilled water. The method of Huggins, et al, *J Exp Med* (1961) 114: 761 was used to assess alkaline phosphatase using polystyrene plates.

K. RESULTS OF HISTOLOGY STUDIES AND BIOCHEMICAL ASSAYS

Partial results are summarized in the table below.

| | SUMMARY: HISTOLOGY AND ALKALINE PHOSPHATASE ACTIVITY BCP/CIS COMBINED WITH CMC-FRACTIONS | | | |
|---|---|---|---|---|
| Group | Cartilage | Bone | Inflammation Round Cells | AP Units/ g w. Tissue (Explants) |
| At Day 14 Post Implantation | | | | |
| R-CMC-B (149:1) | 5+ | 3+ | + | 10.1 |
| R-CMC-B-1 (62:1) | 2+ | 4+ | (+) | 11.5 |
| BCP/CIS (9:1) | 0 | 0 | 4+ | 0.00 |
| At Day 28 Post Implantation | | | | |
| R-CMC-B (148:1) | 3+ | 4+ | ++ | 11.0 |
| R-CMC-B-1 (62:1) | + | 5+ | + | 13.2 |
| BCP/CIS (Carrier alone) | 0 | 0 | 4 | |

The above data show that CMC-B-1 proteins enhance osteoinduction relative to CMC-bound (the total bound fraction) as reflected by a higher rate, quantity, and quality of bone formation. These studies indicate that endochondral bone formation is affected by the purity of the bone-inducing material and the distribution of proteins therein. These studies further suggest that the two proteins identified in the parent application may play roles in the differentiation of cells involved in bone formation and affect rate and relative amounts of cartilage and bone formation.

As indicated, histological and biochemical data of the 14 and 28 days explanted materials demonstrated that reconstituted total CMC-bound (total proteins bound by CMC) and CMC-B-1 induced cartilage and bone formation in all implants. At 14 days cartilage formation was very high with the R-CMC-bound implants and uniformly distributed over the whole implant. Some new bone was formed peripherally. In contrast, R-CMC-B-1 showed only little cartilage and already lots of bone at 14 days. At 28 days R-CMC-bound explants still contained cartilage. (The amount of cartilage and bone appeared to be about the same.) R-CMC-B-1 meanwhile, contained only traces of cartilage and well-developed bone with fatty marrow cavities. All of the latter explants appeared to be larger than usually found. Histological observations were confirmed by biochemical data. Both materials showed high levels of alkaline phosphatase activity. The calcium content at 28 days was very high in both materials (approximately 32 mg Ca/g wet tissue for R-CMC-bound and approximately 39 mg Ca/g wet tissue for R-CMC-B-1).

Inflammation was very low and no giant cell reaction was observed in the R-CMC-bound and R-CMC-B-1 explants at either time point.

The claimed osteogenic material may be used as the active ingredient of osteogenic implant compositions for repairing, replacing, or augmenting bone tissue in living mammals, including man. Osteogenically effective amounts of the material will normally be formulated with pharmacologically and physiologically acceptable solid carriers such as BCP for implantation. The weight ratio of active protein to carrier will typically be in the range of 1:50 to 1:1000. The implants may be placed at a predetermined site in the patient by conventional surgical techniques.

The claimed factor may also be useful for treating bone deficiencies, such as osteoporosis and osteopetrosis, systemically. For such treatment the proteins will be formulated in therapeutically effective amounts with injectable carriers and administered parenterally to the patient.

Modifications of the above-described modes for carrying out the invention that are obvious to those of skill in the fields of biochemistry, medicine, and related fields are intended to be within the scope of the following claims.

We claim:

1. A process for preparing a partially purified bone-inducing factor which comprises:
    (a) treating demineralized bone with a chaotropic extractant that solubilizes nonfibrous proteins;
    (b) subjecting the extract from step (a) to gel filtration to recover a fraction containing proteins of molecular weight 10,000–30,000;
    (c) adsorbing the fraction from step (b) onto a carboxymethyl cellulose cation exchanger at approximately pH 4.5–5.5; and
    (d) eluting an osteogenically active fraction from the cation exchanger with a sodium chloride gradient of about 10 mM to about 150 mM in the presence of a nonionic chaotropic agent.

2. The method of claim 1 wherein the extractant is guanidine hydrochloride and the pH is about 4.8.

3. A partially purified bone-inducing factor prepared by the process of claim 1.

4. A partially purified bone-inducing factor prepared by the process of claim 2.

5. An osteogenic implant material comprising:
    (a) an osteogenically effective amount of a factor of claim 1 reconstituted with
    (b) a substantially nonimmunogenic carrier.

6. An osteogenic implant material comprising:
    (a) an osteogenically effective amount of a factor of claim 2 reconstituted with
    (b) a substantially nonimmunogenic carrier.

7. A method of inducing bone formation at a predetermined site in a living mammal comprising implanting the material of claim 5 at said site.

8. A method of inducing bone formation at a predetermined site in a living mammal comprising implanting the material of claim 6 at said site.

* * * * *